(12) United States Patent
Fang et al.

(10) Patent No.: US 11,634,720 B2
(45) Date of Patent: Apr. 25, 2023

(54) YEAST PRODUCING TYROSOL OR HYDROXYTYROSOL, AND CONSTRUCTION METHODS THEREOF

(71) Applicant: SHANDONG HENGLU BIOTECH. CO., LTD, Shandong (CN)

(72) Inventors: Xu Fang, Jinan (CN); Wei Guo, Jinan (CN); Lijuan Han, Jinan (CN)

(73) Assignee: SHANDONG HENGLU BIOTECH. CO., LTD., Jinan (CN)

( * ) Notice: Subject to any disclaimer, the term of this patent is extended or adjusted under 35 U.S.C. 154(b) by 82 days.

(21) Appl. No.: 17/053,983

(22) PCT Filed: Apr. 16, 2019

(86) PCT No.: PCT/CN2019/082883
§ 371 (c)(1),
(2) Date: Nov. 9, 2020

(87) PCT Pub. No.: WO2019/237824
PCT Pub. Date: Dec. 19, 2019

(65) Prior Publication Data
US 2021/0254081 A1    Aug. 19, 2021

(30) Foreign Application Priority Data

Jun. 12, 2018 (CN) .......................... 201810601213.8

(51) Int. Cl.
| | | |
|---|---|---|
| C12N 15/81 | (2006.01) | |
| C12N 9/88 | (2006.01) | |
| C12N 15/52 | (2006.01) | |
| C12P 7/22 | (2006.01) | |

(52) U.S. Cl.
CPC ............... *C12N 15/81* (2013.01); *C12N 9/88* (2013.01); *C12N 15/52* (2013.01); *C12P 7/22* (2013.01); *C12Y 101/01001* (2013.01); *C12Y 401/01025* (2013.01)

(58) Field of Classification Search
CPC .......... C12N 15/81; C12N 9/88; C12N 15/52; C12N 9/0006; C12P 7/22; C12Y 101/01001; C12Y 401/01025
See application file for complete search history.

(56) References Cited

U.S. PATENT DOCUMENTS

2015/0232863 A1    8/2015    Argyros et al.

FOREIGN PATENT DOCUMENTS

| CN | 104099379 A | 10/2014 |
| CN | 104805110 A | 7/2015 |
| CN | 104946575 A | 9/2015 |
| CN | 107586794 A | 1/2018 |
| CN | 108753636 A | 11/2018 |
| CN | 106754607 B | 11/2019 |

OTHER PUBLICATIONS

Jiang et al. Metabolic engineering of *Saccharomyces cerevisiae* for high-level production of salidroside from glucose. J. Agric. Food Chem. (2018), 66: 4431-4438. (Year: 2018).*
Li et al. Establishing an artificial pathway for efficient biosynthesis of hydroxytyrosol. ACS Synth. Biol. 2018, 7: 647-654, Epub Dec. 28, 2017. (Year: 2017).*
Gold et al. (Metabolic engineering of a tyrosine-overproducing yeast platform using targeted metabolomics. Microbial Cell Factories (2015): 14: 73. (Year: 2015).*
Hisayoshi Soejima et al., "Breeding of a high tyrosol-producing sake yeast by isolation of an ethanol-resistant mutant from a trp3 mutant" J. Inst. Brew, vol. 118, pp. 264-268, 2012.
Jun. 28, 2019 International Search Report issued in International Patent Application No. PCT/CN2019/082883.

* cited by examiner

*Primary Examiner* — Iqbal H Chowdhury
(74) *Attorney, Agent, or Firm* — Oliff PLC (57) ABSTRACT

The technical field of preparation of organic compounds, and particularly to yeasts producing tyrosol or hydroxytyrosol and construction methods thereof. PcAAS and ADH-encoding DNA sequences are introduced into the yeast strain BY4741, to obtain a PcAAS-ADH recombinant yeast producing tyrosol. A PDC1 knockout cassette and a TyrA expression cassette are introduced into the PcAAS-ADH recombinant yeast to obtain a PcAAS-ADH-ΔPDC1-TyrA recombinant yeast producing tyrosol. A HpaBC encoding DNA sequence is introduced into the PcAAS-ADH-ΔPDC1-TyrA recombinant yeast, to obtain a PcAAS-ADH-HpaBC-ΔPDC1-TyrA recombinant yeast producing hydroxytyrosol. The construction of a tyrosol or hydroxytyrosol biosynthesis pathway in the yeast strain BY4741 enhances the production of tyrosol or hydroxytyrosol.

7 Claims, 1 Drawing Sheet
Specification includes a Sequence Listing.

```
                          SEQUENCE LISTING

<160> NUMBER OF SEQ ID NOS: 26

<210> SEQ ID NO 1
<211> LENGTH: 514
<212> TYPE: PRT
<213> ORGANISM: Artificial Sequence
<220> FEATURE:
<223> OTHER INFORMATION: synthetic construct

<400> SEQUENCE: 1

Met Gly Ser Ile Asp Asn Leu Thr Glu Lys Leu Ala Ser Gln Phe Pro
1               5                   10                  15

Met Asn Thr Leu Glu Pro Glu Gly Phe Arg Arg Gln Gly His Met Met
            20                  25                  30

Ile Asp Phe Leu Ala Asp Tyr Tyr Arg Lys Val Glu Asn Tyr Pro Val
        35                  40                  45

Arg Ser Gln Val Ser Pro Gly Tyr Leu Arg Glu Ile Leu Pro Glu Ser
    50                  55                  60

Ala Pro Tyr Asn Pro Glu Ser Leu Glu Thr Ile Leu Gln Asp Val Gln
65                  70                  75                  80

Thr Lys Ile Ile Pro Gly Ile Thr His Trp Gln Ser Pro Asn Phe Phe
                85                  90                  95

Ala Tyr Phe Pro Ser Ser Gly Ser Thr Ala Gly Phe Leu Gly Glu Met
            100                 105                 110

Leu Ser Thr Gly Phe Asn Val Val Gly Phe Asn Trp Met Val Ser Pro
        115                 120                 125

Ala Ala Thr Glu Leu Glu Asn Val Val Thr Asp Trp Phe Gly Lys Met
    130                 135                 140

Leu Gln Leu Pro Lys Ser Phe Leu Phe Ser Gly Gly Gly Gly Gly Val
145                 150                 155                 160

Leu Gln Gly Thr Thr Cys Glu Ala Ile Leu Cys Thr Leu Val Ala Ala
                165                 170                 175

Arg Asp Lys Asn Leu Arg Gln His Gly Met Asp Asn Ile Gly Lys Leu
            180                 185                 190

Val Val Tyr Cys Ser Asp Gln Thr His Ser Ala Leu Gln Lys Ala Ala
        195                 200                 205

Lys Ile Ala Gly Ile Asp Pro Lys Asn Phe Arg Ala Ile Glu Thr Thr
    210                 215                 220

Lys Ser Ser Asn Phe Gln Leu Cys Pro Lys Arg Leu Glu Ser Ala Ile
225                 230                 235                 240

Leu His Asp Leu Gln Asn Gly Leu Ile Pro Leu Tyr Leu Cys Ala Thr
                245                 250                 255

Val Gly Thr Thr Ser Ser Thr Thr Val Asp Pro Leu Pro Ala Leu Thr
            260                 265                 270

Glu Val Ala Lys Lys Tyr Asp Leu Trp Val His Val Asp Ala Ala Tyr
        275                 280                 285

Ala Gly Ser Ala Cys Ile Cys Pro Glu Phe Arg Gln Tyr Leu Asp Gly
    290                 295                 300

Val Glu Asn Ala Asp Ser Phe Ser Leu Asn Ala His Lys Trp Phe Leu
305                 310                 315                 320

Thr Thr Leu Asp Cys Cys Cys Leu Trp Val Arg Asn Pro Ser Ala Leu
```

```
                    325                 330                 335
Ile Lys Ser Leu Ser Thr Tyr Pro Glu Phe Leu Lys Asn Asn Ala Ser
            340                 345                 350

Glu Thr Asn Lys Val Val Asp Tyr Lys Asp Trp Gln Ile Met Leu Ser
            355                 360                 365

Arg Arg Phe Arg Ala Leu Lys Leu Trp Phe Val Leu Arg Ser Tyr Gly
        370                 375                 380

Val Gly Gln Leu Arg Glu Phe Ile Arg Gly His Val Gly Met Ala Lys
385                 390                 395                 400

Tyr Phe Glu Gly Leu Val Asn Met Asp Lys Arg Phe Glu Val Val Ala
                405                 410                 415

Pro Arg Leu Phe Ser Met Val Cys Phe Arg Ile Lys Pro Ser Ala Met
            420                 425                 430

Ile Gly Lys Asn Asp Glu Asp Glu Val Asn Glu Ile Asn Arg Lys Leu
            435                 440                 445

Leu Glu Ser Val Asn Asp Ser Gly Arg Ile Tyr Val Ser His Thr Val
450                 455                 460

Leu Gly Gly Ile Tyr Val Ile Arg Phe Ala Ile Gly Gly Thr Leu Thr
465                 470                 475                 480

Asp Ile Asn His Val Ser Ala Ala Trp Lys Val Leu Gln Asp His Ala
                485                 490                 495

Gly Ala Leu Leu Asp Asp Thr Phe Thr Ser Asn Lys Leu Val Glu Val
            500                 505                 510

Leu Ser

<210> SEQ ID NO 2
<211> LENGTH: 1545
<212> TYPE: DNA
<213> ORGANISM: Artificial Sequence
<220> FEATURE:
<223> OTHER INFORMATION: synthetic construct

<400> SEQUENCE: 2
atgggttcca ttgataactt gaccgaaaag ttggcttctc agtttccaat gaataccttg      60
gaaccagaag aattcagacg tcaaggtcat atgatgattg atttcttggc cgactactac     120
agaaaggttg aaaattaccc agtcaggtca caagtttctc aggttatttt gagagaaatc     180
ttgccagaat ctgctccata caatccagaa tctttggaaa ctatcttgca ggacgttcag     240
accaagatta ttccaggtat tactcattgg cagtccccaa atttctttgc ttactttcca     300
tcttcaggtt ctactgctgg ttttttgggt gaaatgttgt ctactggttt caacgttgtt     360
ggctttaact ggatggtttc accagctgct actgaattgg aaaacgttgt tactgattgg     420
ttcggtaaga tgttgcaatt gccaaagtct tccttgtttt caggtggtgg tggcggtgtt     480
ttacaaggta ctacttgtga agctattttg tgcactttgg ttgctgctag agataagaac     540
ttgagacaac atggtatgga caacatcggt aagttggttg tttactgttc tgatcaaact     600
cactctgcct tgcaaaaagc tgctaaaatt gctggtattg acccaaagaa cttcagagct     660
attgaaacca ccaagtcctc taactttcaa ttgtgtccaa agagattgga gtctgcaatc     720
ttgcatgact gcaaaatgg tttgattccc ttgtacttgt gtgctactgt ggtactaca     780 tcttctacta ctgttgatcc attgccagct ttgactgaag ttgctaaaaa gtacgatttg     840
tgggttcatg ttgatgctgc ttatgctggt tctgcttgta tttgtccaga gttcagacaa     900
tacttggatg gtgttgaaaa cgccgattct tttctcttga atgcccataa gtggttcttg     960
```

```
actactttgg actgttgttg cttgtgggtt agaaatccat ctgccttgat taagtccttg    1020
tctacttacc cagaattctt gaagaacaac gcctctgaaa ctaacaaggt tgttgattac    1080
aaggactggc agatcatgtt gtcaagaaga ttcagagctt taaagttgtg gttcgtcttg    1140
agatcttatg tgttggtca attgagagaa ttcatcagag gtcatgttgg tatggctaag    1200
tactttgaag gtttggttaa catggacaag agattcgaag ttgttgctcc taggttgttc    1260
tctatggttt gttttagaat caagccctcc gctatgattg gtaagaatga tgaagatgaa    1320
gtcaacgaga tcaaccgtaa gctattggaa tccgttaatg actctggtag gatctacgtt    1380
tctcatacag ttttaggtgg tatctacgtt atcagattcg ctattggtgg tactttgacc    1440
gatatcaatc atgtttctgc tgcttggaag gtattacaag atcatgctgg tgctttgttg    1500
gatgatactt tcacttctaa caagttggtc gaggtcttgt cttaa                   1545
```

<210> SEQ ID NO 3
<211> LENGTH: 362
<212> TYPE: PRT
<213> ORGANISM: Artificial Sequence
<220> FEATURE:
<223> OTHER INFORMATION: synthetic construct

<400> SEQUENCE: 3

```
Met Gln Val Lys Ala Ala Val Thr Leu Gly Tyr Gln Gln Pro Phe Val
1               5                   10                  15

Ile Lys Asp Val Glu Val Ala Pro Pro Gly Lys Asp Glu Ile Leu Val
                20                  25                  30

Lys Ile Val Ala Thr Gly Val Cys His Thr Asp Ala Val Met Arg Asp
            35                  40                  45

Asn Pro Gly Val Val Pro Met Pro Ala Ile Leu Gly His Glu Gly Ala
        50                  55                  60

Gly Ile Val Ala Ser Val Gly Glu Ala Val Ser Gly Ile Arg Val Gly
65                  70                  75                  80

Asp His Val Val Leu Ser Tyr Ala Ala Cys His His Cys Glu Asn Cys
                85                  90                  95

Leu Ser Asn His Pro Ser Ala Cys Glu Asp Phe Asn Thr Leu Asn Phe
                100                 105                 110

Gly Gly Arg Arg Glu Asp Gly Thr Thr Pro Tyr Arg Leu Glu Asp Gln
            115                 120                 125

Asp Leu Ser Leu Phe Phe Gly Gln Ser Ser Phe Ser Gln Tyr Val Val
        130                 135                 140

Thr Arg Ala Ser Asn Ala Val Val Asp Pro Glu Val Asp Leu Thr
145                 150                 155                 160

Leu Leu Gly Pro Leu Gly Cys Gly Ile Gln Thr Gly Ser Gly Thr Val
                165                 170                 175

Leu Asn Arg Leu Lys Pro Val Val Gly Glu Ser Leu Val Val Phe Gly
                180                 185                 190

Cys Gly Ala Val Gly Leu Ser Ala Ile Met Ala Ala Lys Leu Thr Gly
            195                 200                 205

Cys Ser Gln Ile Ile Ala Val Asp Ile His Ala Ser Arg Leu Ala Leu
        210                 215                 220

Ala Gly Glu Leu Gly Ala Thr His Gln Ile Asn Gly Lys Glu Gln Asp
225                 230                 235                 240

Ala Val Ala Val Ile Lys Gln Ile Thr Gly Lys Gly Ala His Tyr Ala
                245                 250                 255

Val Glu Thr Thr Gly Val Ser Ala Ile Val Leu Gln Ala Val His Ala
```

```
                260                 265                 270
Val Lys Pro Leu Gly Thr Val Ala Ile Val Gly Phe Thr Gly Asp Ile
            275                 280                 285

Thr Leu Asn Val Gln Asn Asp Leu Met Ala Glu Gly Lys Ser Leu Val
        290                 295                 300

Gly Val Ile Glu Gly Asp Ala Val Pro Ala Leu Phe Ile Pro Leu Leu
305                 310                 315                 320

Val Gln Leu Tyr Lys Gln Gly Lys Phe Pro Ile Asp Lys Leu Ile Ala
                325                 330                 335

Arg Tyr Pro Leu Ala Asp Ile Asn Gln Ala Phe Ala Asp Ser Ala Ser
            340                 345                 350

Gly Lys Val Ile Lys Pro Val Val Val Met
            355                 360

<210> SEQ ID NO 4
<211> LENGTH: 1089
<212> TYPE: DNA
<213> ORGANISM: Artificial Sequence
<220> FEATURE:
<223> OTHER INFORMATION: synthetic construct

<400> SEQUENCE: 4
atgcaagtta aggctgctgt tactttgggt taccaacaac cattcgttat caaggatgtt      60
gaagttgctc caccaggtaa agacgaaatt ttggttaaga tagttgctac cggtgtttgt     120
catactgatg ctgttatgag agataaccca ggtgttgttc aatgccagc tatttttgggt    180
catgaaggtc tggtatagt tgcttctgtt ggtgaagctg tttctggtat tagagttggt     240
gatcacgttg ttttgtctta cgctgcttgt catcattgtg aaaactgctt gtctaatcat     300
ccatctgctt gcgaagattt caacactttg aatttcggtg gtagaagaga agatggtact     360
actccatata gattggaaga tcaggacctg tctttgttct ttggtcaatc ttctttctcc     420
caatacgttg ttactagagc ttctaacgct gttgttgttg atccagaagt tgatttgact     480
ttgttgggtc cattaggttg tggtattcaa actggttctg gtactgtttt gaacagattg     540
aaaccagttg tcggtgaatc cttggttgtt tttggttgtg gtgctgttgg tttgtctgct     600
attatggctg ctaaattgac tggttgctcc caaattattg ccgttgatat tcatgcttcc     660
agattggctt tggctggtga attgggtgct actcatcaaa tcaatggtaa agaacaagat     720
gccgttgccg tcattaagca aattactggt aaaggtgctc attacgctgt tgaaactact     780
ggtgtttctg ctatcgtttt acaagctgtt catgctgtta agccattggg tactgttgct     840
atagttggtt tcactggtga tattaccttg aacgtccaaa acgatttgat ggccgaaggt     900
aaatctttgg ttggtgttat tgaaggtgat gcagttccag cttttgttcat tccattattg    960
gttcagttgt acaagcaagg caagttccca attgataagt tgattgctag atacccattg    1020
gccgatatca atcaagcttt tgctgattct gcttccggta aggttattaa gccagttgtt    1080
gttatgtaa                                                            1089

<210> SEQ ID NO 5
<211> LENGTH: 520
<212> TYPE: PRT
<213> ORGANISM: Artificial Sequence
<220> FEATURE:
<223> OTHER INFORMATION: synthetic construct

<400> SEQUENCE: 5

Met Lys Pro Glu Asp Phe Arg Ala Ser Thr Gln Arg Pro Phe Thr Gly
```

-continued

```
1               5                   10                  15
Glu Glu Tyr Leu Lys Ser Leu Gln Asp Gly Arg Glu Ile Tyr Ile Tyr
            20                  25                  30
Gly Glu Arg Val Lys Asp Val Thr Thr His Pro Ala Phe Arg Asn Ala
            35                  40                  45
Ala Ala Ser Val Ala Gln Leu Tyr Asp Ala Leu His Lys Pro Glu Met
            50                  55                  60
Gln Asp Ser Leu Cys Trp Asn Thr Asp Thr Gly Ser Gly Gly Tyr Thr
65                  70                  75                  80
His Lys Phe Phe Arg Val Ala Lys Ser Ala Asp Asp Leu Arg His Glu
                85                  90                  95
Arg Asp Ala Ile Ala Glu Trp Ser Arg Leu Ser Tyr Gly Trp Met Gly
            100                 105                 110
Arg Thr Pro Asp Tyr Lys Ala Ala Phe Gly Cys Ala Leu Gly Gly Thr
            115                 120                 125
Pro Gly Phe Tyr Gly Gln Phe Glu Gln Asn Ala Arg Asn Trp Tyr Thr
            130                 135                 140
Arg Ile Gln Glu Thr Gly Leu Tyr Phe Asn His Ala Ile Val Asn Pro
145                 150                 155                 160
Pro Ile Asp Arg His Leu Pro Thr Asp Lys Val Lys Asp Val Tyr Ile
                165                 170                 175
Lys Leu Glu Lys Glu Thr Asp Ala Gly Ile Ile Val Ser Gly Ala Lys
            180                 185                 190
Val Val Ala Thr Asn Ser Ala Leu Thr His Tyr Asn Met Ile Gly Phe
            195                 200                 205
Gly Ser Ala Gln Val Met Gly Glu Asn Pro Asp Phe Ala Leu Met Phe
            210                 215                 220
Val Ala Pro Met Asp Ala Asp Gly Val Lys Leu Ile Ser Arg Ala Ser
225                 230                 235                 240
Tyr Glu Met Val Ala Gly Ala Thr Gly Ser Pro Tyr Asp Tyr Pro Leu
                245                 250                 255
Ser Ser Arg Phe Asp Glu Asn Asp Ala Ile Leu Val Met Asp Asn Val
            260                 265                 270
Leu Ile Pro Trp Glu Asn Val Leu Leu Tyr Arg Asp Phe Asp Arg Cys
            275                 280                 285
Arg Arg Trp Thr Met Glu Gly Gly Phe Ala Arg Met Tyr Pro Leu Gln
            290                 295                 300
Ala Cys Val Arg Leu Ala Val Lys Leu Asp Phe Ile Thr Ala Leu Leu
305                 310                 315                 320
Lys Lys Ser Leu Glu Cys Thr Gly Thr Leu Glu Phe Arg Gly Val Gln
                325                 330                 335
Ala Asp Leu Gly Glu Val Val Ala Trp Arg Asn Thr Phe Trp Ala Leu
            340                 345                 350
Ser Asp Ser Met Cys Ser Glu Ala Thr Pro Trp Val Asn Gly Ala Tyr
            355                 360                 365
Leu Pro Asp His Ala Ala Leu Gln Thr Tyr Arg Val Leu Ala Pro Met
            370                 375                 380
Ala Tyr Ala Lys Ile Lys Asn Ile Ile Glu Arg Asn Val Thr Ser Gly
385                 390                 395                 400
Leu Ile Tyr Leu Pro Ser Ser Ala Arg Asp Leu Asn Asn Pro Gln Ile
                405                 410                 415
Asp Gln Tyr Leu Ala Lys Tyr Val Arg Gly Ser Asn Gly Met Asp His
            420                 425                 430
```

Val Gln Arg Ile Lys Ile Leu Lys Leu Met Trp Asp Ala Ile Gly Ser
        435                 440                 445

Glu Phe Gly Gly Arg His Glu Leu Tyr Glu Ile Asn Tyr Ser Gly Ser
    450                 455                 460

Gln Asp Glu Ile Arg Leu Gln Cys Leu Arg Gln Ala Gln Ser Ser Gly
465                 470                 475                 480

Asn Met Asp Lys Met Met Ala Met Val Asp Arg Cys Leu Ser Glu Tyr
                485                 490                 495

Asp Gln Asn Gly Trp Thr Val Pro His Leu His Asn Asn Asp Asp Ile
                500                 505                 510

Asn Met Leu Asp Lys Leu Leu Lys
            515                 520

<210> SEQ ID NO 6
<211> LENGTH: 1563
<212> TYPE: DNA
<213> ORGANISM: Artificial Sequence
<220> FEATURE:
<223> OTHER INFORMATION: synthetic construct

<400> SEQUENCE: 6
atgaaaccag aagatttccg cgccagtacc aacgtccgt tcaccgggga agagtatctg      60
aaaagcctgc aggatggtcg cgagatctat atctatggcg agcgagtgaa agacgtcact    120
actcatccgg catttcgtaa tgcggctgcg tctgttgccc aactgtacga cgcgctacac    180
aaaccggaga tgcaggactc tctgtgctgg aacaccgaca ccggcagcgg cggctatacc    240
cataaattct ccgcgtggc gaaaagtgcc gacgacctgc ccacgaacg cgatgccatc      300 gctgagtggt cacgcctgag ctatggctgg atgggccgta ccccagacta caaagctgct    360
ttcggttgcg cactgggcgg aactccgggc ttttacggtc agttcgagca gaacgcccgt    420
aactggtaca cccgtattca ggaaactggc ctctacttta ccacgcgat gttaaccca     480 ccgatcgatc gtcatttgcc gaccgataaa gtaaagacg tttacatcaa gctggaaaaa     540
gagactgacg ccgggattat cgtcagcggt gcgaaagtgg ttgccaccaa ctcggcgctg    600
actcactaca catgattgg cttcggctcg cacaagtaa tgggcgaaaa cccggacttc     660
gcactgatgt tcgttgcgcc aatggatgcc gatggcgtca aattaatctc ccgcgcctct    720
tatgagatgg tcgcgggtgc taccggctca ccgtatgact accgctctc cagccgcttc    780 gatgagaacg atgcgattct ggtgatggat aacgtgctga tcccatggga aaacgtgctg    840
ctctaccgcg attttgatcg ctgccgtcgc tggacgatgg aaggcggttt cgcccgtatg    900
tatccgctgc aagcctgtgt gcgcctggca gtgaaactcg acttcattac ggcactgctg    960
aaaaaatcac tcgaatgtac cggcacctg gagttccgtg tgtgcaggc cgatctcggt     1020 gaagtggtgg cgtggcgcaa cacacttctgg gcattgagtg actcgatgtg ttctgaagcg    1080
acgccgtggg tcaacggggc ttatttaccg gatcatgccg cactgcaaac ctatcgcgta    1140
ctggcaccaa tggcctacgc gaagatcaaa aacattatcg aacgcaacgt taccagtggc    1200
ctgatctatc tcccttccag tgcccgtgac ctgaacaatc gcagatcga ccagtatctg    1260 gcgaagtatg tgcgcggttc gaacggtatg atcacgtcc agcgcatcaa gatcctcaaa    1320
ctgatgtggg atgccattgg cagcgagttt ggtggtcgtc acgaactgta tgaaatcaac    1380
tactccggta gccaggatga gattcgcctg cagtgtctgc gccaggcaca agctccggc     1440 aatatggaca gatgatggc gatggttgat cgctgcctgt cggaatacga ccagaacggc    1500

```
tggactgtgc cgcacctgca caacaacgac gatatcaaca tgctggataa gctgctgaaa    1560
taa                                                                 1563
```

<210> SEQ ID NO 7
<211> LENGTH: 170
<212> TYPE: PRT
<213> ORGANISM: Artificial Sequence
<220> FEATURE:
<223> OTHER INFORMATION: synthetic construct

<400> SEQUENCE: 7

```
Met Gln Leu Asp Glu Gln Arg Leu Arg Phe Arg Asp Ala Met Ala Ser
1               5                   10                  15

Leu Ser Ala Ala Val Asn Ile Ile Thr Thr Glu Gly Asp Ala Gly Gln
            20                  25                  30

Cys Gly Ile Thr Ala Thr Ala Val Cys Ser Val Thr Asp Thr Pro Pro
        35                  40                  45

Ser Leu Met Val Cys Ile Asn Ala Asn Ser Ala Met Asn Pro Val Phe
    50                  55                  60

Gln Gly Asn Gly Lys Leu Cys Val Asn Val Leu Asn His Glu Gln Glu
65                  70                  75                  80

Leu Met Ala Arg His Phe Ala Gly Met Thr Gly Met Ala Met Glu Glu
                85                  90                  95

Arg Phe Ser Leu Ser Cys Trp Gln Lys Gly Pro Leu Ala Gln Pro Val
            100                 105                 110

Leu Lys Gly Ser Leu Ala Ser Leu Glu Gly Glu Ile Arg Asp Val Gln
        115                 120                 125

Ala Ile Gly Thr His Leu Val Tyr Leu Val Glu Ile Lys Asn Ile Ile
    130                 135                 140

Leu Ser Ala Glu Gly His Gly Leu Ile Tyr Phe Lys Arg Arg Phe His
145                 150                 155                 160

Pro Val Met Leu Glu Met Glu Ala Ala Ile
                165                 170
```

<210> SEQ ID NO 8
<211> LENGTH: 513
<212> TYPE: DNA
<213> ORGANISM: Artificial Sequence
<220> FEATURE:
<223> OTHER INFORMATION: synthetic construct

<400> SEQUENCE: 8

```
atgcaattag atgaacaacg cctgcgcttt cgtgacgcaa tggccagcct gtcggcagcg     60
gtaaatatta tcaccaccga gggcgacgcc ggacaatgcg ggattacggc aacggccgtc    120
tgctcggtca cggatacacc accatcgctg atggtgtgca ttaacgccaa cagtgcgatg    180
aacccggttt ttcagggcaa cggtaagttg tgcgtcaacg tcctcaacca tgagcaggaa    240
ctgatggcac gccacttcgc gggcatgaca ggcatggcga tggaagagcg ttttagcctc    300
tcatgctggc aaaaaggtcc gctggcgcag ccggtgctaa aaggttcgct ggccagtctt    360
gaaggtgaga tccgcgatgt gcaggcaatt ggcacacatc tggtgtatct ggtggagatt    420
aaaaacatca tcctcagtgc agaaggtcac ggacttatct actttaaacg ccgtttccat    480
ccggtgatgc tggaaatgga agctgcgatt taa                                 513
```

<210> SEQ ID NO 9
<211> LENGTH: 50
<212> TYPE: DNA

```
<213> ORGANISM: Artificial Sequence
<220> FEATURE:
<223> OTHER INFORMATION: primer

<400> SEQUENCE: 9
aagcgtgaca taactaatta catgattaag acaagacctc gaccaacttg      50

<210> SEQ ID NO 10
<211> LENGTH: 50
<212> TYPE: DNA
<213> ORGANISM: Artificial Sequence
<220> FEATURE:
<223> OTHER INFORMATION: primer

<400> SEQUENCE: 10
gaataaacac acataaacaa acaaaatggg ttccattgat aacttgaccg      50

<210> SEQ ID NO 11
<211> LENGTH: 50
<212> TYPE: DNA
<213> ORGANISM: Artificial Sequence
<220> FEATURE:
<223> OTHER INFORMATION: primer

<400> SEQUENCE: 11
ttttaattac aaaggatcct ctagaatgca agttaaggct gctgttactt      50

<210> SEQ ID NO 12
<211> LENGTH: 50
<212> TYPE: DNA
<213> ORGANISM: Artificial Sequence
<220> FEATURE:
<223> OTHER INFORMATION: primer

<400> SEQUENCE: 12
tctatcgatt tcaattcaat tcaatttaca taacaacaac tggcttaata      50

<210> SEQ ID NO 13
<211> LENGTH: 25
<212> TYPE: DNA
<213> ORGANISM: Artificial Sequence
<220> FEATURE:
<223> OTHER INFORMATION: primer

<400> SEQUENCE: 13
ttatgtatgc tcttctgact tttcg                                 25

<210> SEQ ID NO 14
<211> LENGTH: 50
<212> TYPE: DNA
<213> ORGANISM: Artificial Sequence
<220> FEATURE:
<223> OTHER INFORMATION: primer

<400> SEQUENCE: 14
gggacgaggc aagctaaaca gatcttttga ttgatttgac tgtgttattt      50

<210> SEQ ID NO 15
<211> LENGTH: 50
<212> TYPE: DNA
<213> ORGANISM: Artificial Sequence
<220> FEATURE:
<223> OTHER INFORMATION: primer

<400> SEQUENCE: 15
aaataacaca gtcaaatcaa tcaaaagatc tgtttagctt gcctcgtccc      50
```

<210> SEQ ID NO 16
<211> LENGTH: 50
<212> TYPE: DNA
<213> ORGANISM: Artificial Sequence
<220> FEATURE:
<223> OTHER INFORMATION: primer

<400> SEQUENCE: 16
tataaaactt taactaataa ttagagagag ctcgttttcg acactggatg          50

<210> SEQ ID NO 17
<211> LENGTH: 50
<212> TYPE: DNA
<213> ORGANISM: Artificial Sequence
<220> FEATURE:
<223> OTHER INFORMATION: primer

<400> SEQUENCE: 17
catccagtgt cgaaaacgag ctctctctaa ttattagtta aagttttata          50

<210> SEQ ID NO 18
<211> LENGTH: 23
<212> TYPE: DNA
<213> ORGANISM: Artificial Sequence
<220> FEATURE:
<223> OTHER INFORMATION: primer

<400> SEQUENCE: 18
tttcaatcat tggagcaatc att                                       23

<210> SEQ ID NO 19
<211> LENGTH: 25
<212> TYPE: DNA
<213> ORGANISM: Artificial Sequence
<220> FEATURE:
<223> OTHER INFORMATION: primer

<400> SEQUENCE: 19
ttatgtatgc tcttctgact tttcg                                     25

<210> SEQ ID NO 20
<211> LENGTH: 47
<212> TYPE: DNA
<213> ORGANISM: Artificial Sequence
<220> FEATURE:
<223> OTHER INFORMATION: primer

<400> SEQUENCE: 20
aatgcggtca attcagcaac cattttgatt gatttgactg tgttatt             47

<210> SEQ ID NO 21
<211> LENGTH: 47
<212> TYPE: DNA
<213> ORGANISM: Artificial Sequence
<220> FEATURE:
<223> OTHER INFORMATION: primer

<400> SEQUENCE: 21
aataacacag tcaaatcaat caaaatggtt gctgaattga ccgcatt             47

<210> SEQ ID NO 22
<211> LENGTH: 47
<212> TYPE: DNA
<213> ORGANISM: Artificial Sequence
<220> FEATURE:

-continued

```
<223> OTHER INFORMATION: primer

<400> SEQUENCE: 22
acataactaa ttacatgatt aattaattac tggcgattgt cattcgc        47

<210> SEQ ID NO 23
<211> LENGTH: 47
<212> TYPE: DNA
<213> ORGANISM: Artificial Sequence
<220> FEATURE:
<223> OTHER INFORMATION: primer

<400> SEQUENCE: 23
gcgaatgaca atcgccagta attaattaat catgtaatta gttatgt        47

<210> SEQ ID NO 24
<211> LENGTH: 25
<212> TYPE: DNA
<213> ORGANISM: Artificial Sequence
<220> FEATURE:
<223> OTHER INFORMATION: primer

<400> SEQUENCE: 24
tttcaatcat tggagcaatc atttt                                25

<210> SEQ ID NO 25
<211> LENGTH: 25
<212> TYPE: DNA
<213> ORGANISM: Artificial Sequence
<220> FEATURE:
<223> OTHER INFORMATION: primer

<400> SEQUENCE: 25
cggtcttcaa tttctcaagt ttcag                                25

<210> SEQ ID NO 26
<211> LENGTH: 25
<212> TYPE: DNA
<213> ORGANISM: Artificial Sequence
<220> FEATURE:
<223> OTHER INFORMATION: primer

<400> SEQUENCE: 26
gcaattaatg tgagttagct cactc                                25
```

YEAST PRODUCING TYROSOL OR HYDROXYTYROSOL, AND CONSTRUCTION METHODS THEREOF

BACKGROUND

The present application contains a Sequence Listing that has been submitted electronically in ASCII format and is hereby incorporated by reference in its entirety. The ASCII copy, created on Apr. 6, 2021, is named Substitute Sequence Listing_ST25.txt and is 24,155 bytes in size.

TECHNICAL FIELD

The present invention relates to the technical field of bioengineering, and particularly to a genetically recombinant yeast for high-level production of tyrosol, a *Saccharomyces cerevisiae* strain for heterologous synthesis of hydroxytyrosol, and construction methods thereof.

RELATED ART

Tyrosol is a natural antioxidant derived from olive oil and is a derivative of phenylethanol. Tyrosol is also known as the aglycone of salidroside, one of active ingredients in *Rhodiola rosea*, and is a precursor of salidroside and hydroxytyrosol. It can protect cells from oxidative damage, and is a phenolic compound with important industrial significance. Tyrosol and its derivatives are precursors for synthesizing various organic compounds. Tyrosol can be used in a pharmaceutical preparation. Hydroxytyrosol, a derivative of tyrosol, has a potent antioxidation effect and a variety of physiological and medical functions. Hydroxytyrosol has a more potent antioxidation effect than tyrosol, can be used in the synthesis of many polymers, is known to be non-toxic and widely used in biomedicine, functional foods, and other industries, and can prevent the occurrence of cardiovascular diseases, osteopenia, and other diseases. At present, hydroxytyrosol is mainly obtained by extraction from olive leaves, which has the disadvantages of high cost and occupation of a large amount of arable land.

Among chemical methods for synthesizing tyrosol and hydroxytyrosol, synthesis from phenylethanol mainly includes protection of hydroxyl group, nitration, reduction, diazotization, and hydrolysis to obtain p-hydroxyphenylethanol, with a yield of 70%, but phenylethanol is highly costly and short in supply; synthesis from nitrotoluene is low in cost, but requires too many steps and has a low yield; and synthesis from p-hydroxystyrene, though having a yield of up to 96% and a purity of up to 99%, requires high raw material cost. The use of such chemical methods to prepare tyrosol requires high raw material costs and is not environmentally friendly, which directly restricts the industrial production of tyrosol. Therefore, the biological synthesis of tyrosol and hydroxytyrosol has become a research hotspot.

Tyrosol has a chemical name of 4-(2-Hydroxyethyl)phenol, a molecular formula of $C_8H_{10}O_2$, a molecular weight of 138.164, a CAS number of 501-94-0, and a structural formula of:

Genetically recombinant *E. coli* strains producing tyrosol have been successfully constructed in several patent documents, for example, Patent Application No. 201310133238.7 titled "Method for biosynthesis of tyrosol in *E. coli*, and use thereof";

Patent Application No. 201410115011.4 titled "*E. coli* expression strain highly expressing tyrosol and/or salidroside and icariside D2 and use thereof";

Patent Application No. 201510242626.8 titled "Recombinant *E. coli* producing hydroxytyrosol with glucose, and recombination method and use thereof";

Patent Application No. 201710091999.9 titled "Recombinant strain producing tyrosol and construction method thereof"; and Patent Application No. 201711054680.5 titled "Method for producing tyrosol and hydroxytyrosol by heterologous metabolic pathway".

However, the removal of *E. coli* endotoxin is a major challenge in large-scale industrial production. Endotoxin is a component in the cell wall of Gram-negative bacteria, which is also known as lipopolysaccharide. Lipopolysaccharide is toxic to the human body.

"Methods for the improvement of product yield and production in a microorganism through the addition of alternate electron acceptors" discloses a method for producing glycerol with a recombinant yeast by conversion with an enzyme to regulate the metabolic pathway.

"Breeding of a high tyrosol-producing sake yeast by isolation of an ethanol-resistant mutant from a trp3 mutant" discloses a breeding strategy to produce a new tyrosol-producing sake yeast by the isolation of an ethanol-resistant mutant from a tryptophan nutritional mutant of *Saccharomyces cerevisiae*.

Moreover, the biosynthetic technology for producing tyrosol and hydroxytyrosol with yeast, especially *Saccharomyces cerevisiae*, has not been reported.

SUMMARY

In view of the above problems in the prior art, a first object of the present invention is to provide a yeast producing tyrosol. A recombinant yeast is developed, by constructing a tyrosol biosynthesis pathway in the yeast strain BY4741, knocking out the PDC1 gene fragment in the gene template of the yeast strain BY4741, and weakening the ethanol synthesis pathway in the yeast, to enhance the production of tyrosol. A yeast strain for heterologous biosynthesis of hydroxytyrosol is constructed by introducing genes able to produce tyrosol and further transforming with hydroxylase genes able to produce hydroxytyrosol.

A second object of the present invention is to provide a yeast producing hydroxytyrosol.

A third object of the present invention is to provide a method for constructing a yeast producing tyrosol.

A fourth object of the present invention is to provide a method for constructing a yeast producing hydroxytyrosol.

A fifth object of the present invention is to provide use of the yeast producing tyrosol or the construction method thereof in the production of tyrosol.

A sixth object of the present invention is to provide use of the yeast producing hydroxytyrosol or the construction method thereof in the production of hydroxytyrosol.

To solve the above technical problems, the following technical solutions are employed in the present invention.

A yeast producing tyrosol is provided, which is constructed by introducing a tyrosine decarboxylase (TryDC) PcAAS encoding DNA sequence derived from *Petroselinum* crispum and an alcohol dehydrogenase (ADH) encoding DNA sequence derived from Enterobacteriaceae into the yeast strain BY4741, to obtain a PcAAS-ADH recombinant yeast.

Preferably, the tyrosine decarboxylase has an amino acid sequence as shown in SEQ ID NO. 1; and the tyrosine decarboxylase encoding DNA sequence is as shown in SEQ ID NO. 2, which expresses the amino acid sequence as shown in SEQ ID NO. 1.

Preferably, the alcohol dehydrogenase has an amino acid sequence as shown in SEQ ID NO. 3; and the alcohol dehydrogenase encoding DNA sequence is as shown in SEQ ID NO. 4, which expresses the amino acid sequence as shown in SEQ ID NO. 3.

Preferably, a PDC1 knockout cassette is introduced into the PcAAS-ADH recombinant yeast, to obtain a PcAAS-ADH-ΔPDC1 recombinant yeast.

Further preferably, the PDC1 knockout cassette is constructed through a process comprising specifically the steps of: by using the genome of the yeast strain BY4741 as a template, amplifying an upstream and a downstream 500 bp homology arm of the PDC1 fragment with primers, amplifying the G418 resistant gene fragment with primers, and fusing the upstream and downstream 500 bp homology arms and the G418 resistant gene fragment, to obtain the PDC1 knockout cassette.

Preferably, a TyrA expression cassette is introduced into the PcAAS-ADH-ΔPDC1 recombinant yeast, to obtain a PcAAS-ADH-ΔPDC1-TyrA recombinant yeast.

Further preferably, the TyrA expression cassette is constructed through a process comprising specifically the steps of: by using the genome of the yeast strain BY4741 as a template, amplifying an upstream 500 bp homology arm with primers; by using the PDC1 knockout cassette as a template, amplifying the TyrA fragment with primers; and fusing the upstream 500 bp homology arm and the TyrA fragment to construct the TyrA expression cassette.

A yeast producing hydroxytyrosol is provided, where a cluster of 4-hydroxyphenylacetic hydroxylase (HpaBC) encoding DNA sequences derived from *Escherichia coli* are introduced into the PcAAS-ADH-ΔPDC1-TyrA recombinant yeast producing tyrosol, to obtain a PcAAS-ADH-HpaBC-ΔPDC1-TyrA recombinant yeast producing hydroxytyrosol.

Preferably, the cluster of amino acid sequences of 4-hydroxyphenylacetic hydroxylase comprise an amino acid sequence of 4-hydroxyphenylacetic hydroxylase (HpaB) that is as shown in SEQ ID NO. 5, and an amino acid sequence of 4-hydroxyphenylacetic hydroxylase (HpaC) that is as shown in SEQ ID NO. 7.

Preferably, the DNA sequence encoding 4-hydroxyphenylacetic hydroxylase (HpaB) is as shown in SEQ ID NO. 6, which can express the amino acid sequence as shown in SEQ ID NO. 5; and the DNA sequence encoding 4-hydroxyphenylacetic hydroxylase (HpaC) is as shown in SEQ ID NO. 8, which can express the amino acid sequence as shown in SEQ ID NO. 7.

A method for constructing a yeast producing tyrosol is provided, which comprises specifically the steps of:
1) inserting PcAAS and ADH-encoding DNA sequences into an expression vector, to construct a vector-PcAAS-ADH recombinant expression plasmid;
2) by using the genome of the yeast strain BY4741 as a template, amplifying an upstream and a downstream 500 bp homology arm of the PDC1 fragment with primers, amplifying the G418 resistant gene fragment with primers, and fusing the obtained fragments, to obtain a PDC1 knockout cassette;
3) by using the genome of the yeast strain BY4741 as a template, amplifying an upstream 500 bp homology arm with primers; by using the PDC1 knockout cassette as a template, amplifying the TyrA fragment with primers; and fusing the obtained fragments to construct a TyrA expression cassette; and
4) inserting the PDC1 knockout cassette obtained in Step 2) and the TyrA expression cassette obtained in Step 3) into the vector-PcAAS-ADH recombinant expression plasmid obtained in Step 1), to obtain a PcAAS-ADH-ΔPDC1-TyrA plasmid, and inserting the PcAAS-ADH-ΔPDC1-TyrA plasmid into the yeast strain BY4741, to obtain a recombinant yeast strain PcAAS-ADH-ΔPDC1-TyrA.

The expression vector in Step 1) is preferably pJFE3, pUC19, pδBLE2.0, pGK series vectors, or pXP318.

Further preferably, the vector is pJFE3.

A method for constructing a yeast producing hydroxytyrosol is provided, which comprises specifically the steps of:
1) synthesizing a HpaB and a HpaC encoding gene to construct a HpaBC expression cassette; and
2) introducing the HpaBC expression cassette into the recombinant PcAAS-ADH-ΔPDC1-TyrA yeast, to obtain a recombinant PcAAS-ADH-ΔPDC1-TyrA-HpaBC yeast.

Use of the yeast producing tyrosol and the method for constructing a yeast producing tyrosol in the production of tyrosol is provided.

The use comprises specifically fermenting with the yeast producing tyrosol to obtain tyrosol, where the medium for the fermentation is one or a mixture of glucose, fructose, sucrose, glucose and tyrosine.

Use of the yeast producing hydroxytyrosol and the method for constructing a yeast producing hydroxytyrosol in the production of hydroxytyrosol is provided.

Preferably, the use comprises specifically fermenting with the yeast producing hydroxytyrosol to obtain hydroxytyrosol, where the medium for the fermentation is one or a mixture of glucose, fructose, sucrose, glucose and tyrosine.

The present invention has the following beneficial effects.
1) In this application, a PDC1 knockout cassette is introduced into the PcAAS-ADH recombinant yeast, whereby the ethanol synthesis pathway in yeast is blocked, and the production of tyrosol is enhanced through the metabolic pathway to synthesize tyrosol with PEP.
2) In this application, a TyrA expression cassette is introduced into the PcAAS-ADH-ΔPDC1 recombinant yeast, to make the bidirectional metabolic step of converting PREP into 4HPP unidirectional, thus enhancing the production of tyrosol.
3) In this application, a yeast is developed, by constructing a tyrosol biosynthesis pathway, to enhance the production of tyrosol. A hydroxylase gene that can further convert tyrosol into hydroxytyrosol is introduced to construct a yeast strain heterologously synthesizing hydroxytyrosol. Compared with *E. coli*, *Saccharomyces cerevisiae* has the advantages of high safety, stable production, and high resistance to contamination, thus being suitable for use in large-scale industrial production.
4) The present invention provides a new and environmentally friendly biological preparation technology for tyrosol and hydroxytyrosol, which lays the foundation for large-scale industrial production of tyrosol and hydroxytyrosol, and has important economic value and social benefits.

BRIEF DESCRIPTION OF THE DRAWINGS

The accompanying drawings of this specification constituting a part of this application are used to provide further understanding of this application. The exemplary embodiments and descriptions thereof of this application are intended to explain this application, and do not constitute improper restriction to this application

DETAILED DESCRIPTION

Figure 1:
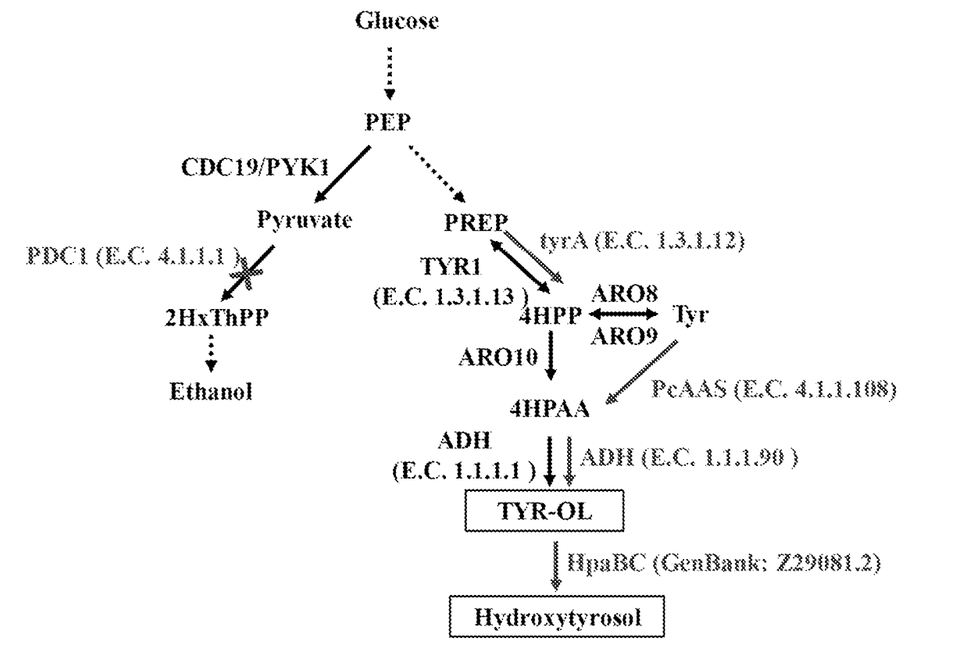
FIG. 1 is a schematic diagram showing a pathway for synthesizing tyrosol and hydroxytyrosol with glucose or tyrosine as a substrate.

It should be noted that the following detailed descriptions are exemplary and are intended to provide further understanding of this application. Unless otherwise indicated, meanings of all technical and scientific terms used in this specification are the same as that usually understood by a person skilled in the technical field to which this application belongs.

It should be noted that, terms used herein are merely used to describe specific implementations, and are not intended to limit exemplary implementations according to this application. As used herein, unless otherwise specified in the context clearly, the singular forms are intended to include the plural forms as well. In addition, it should be further understood that the terms "include", and/or "comprise", when used in this specification, indicate the presence of features, steps, operations, devices, components, and/or combinations thereof.

The present invention is further described below with reference to embodiments:

TABLE 1 shows abbreviations and full names of terms used herein

| Abbreviation | Full name |
|---|---|
|  | Glucose |
| PEP | Phosphoenolpyruvate |
| PREP | Prephenate |
| 2HxThPP | 2-(alpha-Hydroxyethyl) thiamine diphosphate |
| 4HPP | 4-Hydroxyphenylpyruvate |
| Tyr | L-Tyrosine |
| 4HPAA | 4-Hydroxyphenylacetaldehyde |
| TYR-OL | 4-Hydroxyphenylethanol |

Example 1

Construction of pJFE3-PcAAS-ADH Recombinant Expression Plasmid

The amino acid sequences as shown in SEQ ID NO. 1 and SEQ ID NO. 2 were codon-optimized according to the codon preference of the host *Saccharomyces cerevisiae*, to obtain optimized nucleotide sequences corresponding to SEQ ID NO. 1 and SEQ ID NO. 2 for gene synthesis. Amplification using selected primers by KOD FXDNA polymerase available from TOYBO gave the target genes. The bands verified to have a correct size by agarose gel electrophoresis was cut, and the gene fragments were recovered using the OMEGA gel extraction kit. Primers for PCR amplification PcAAS-F sequence as shown in SEQ ID NO. 9; PcAAS-R sequence as shown in SEQ ID NO. 10; adh-F sequence as shown in SEQ ID NO. 11; and adh-R sequence as shown in SEQ ID NO. 12.

Single colonies of *Escherichia coli* strain containing the GBdir+pSC101-BAD-ETgA-tet plasmid on a plate coated with tetracycline as a resistance screening agent were picked into an EP tube containing 1 mL LB liquid medium (sterilized, containing 4 ug/mL tetracycline), and incubated overnight at 30° C. and 200 rpm. The target gene fragments were amplified by high-fidelity KOD FX DNA polymerase and each fragment was ensured to have a 50 bp homologous sequence with the adjacent fragment. The PCR products were subjected to gel electrophoresis and then recovered using a DNA fragment extraction kit. The DNA concentration was determined. Then the fusion fragments were amenable to RED/ET recombination as follows:

(1) 40 μL of the culture incubated overnight was pipetted to 1 mL of fresh LB medium containing 4 μg/mL tetracycline and shaken at 30° C. and 200 rpm for 2 h.

(2) The fragments were ligated using T4 DNA polymerase. The reaction system is shown in Table 2:

TABLE 2

| Reaction system | |
|---|---|
| Component | Amount (uL) |
| DNA fragment | 500 ng each |
| 10 × NE Buffer 2 | 2 |
| 100 × BSA Buffer | 0.2 |
| T4 DNA polymerase | 0.13 |
| dd H$_2$O | q.s. to 20 μl |
| In total | 20 |

The above reagents were added to a PCR tube and reacted under conditions as shown in Table 3.

TABLE 3

| Reaction conditions | |
|---|---|
| Reaction temperature | Reaction time |
| 25° C. | 60 min |
| 75° C. | 20 min |
| 50° C. | 30 min |
| 4° C. | ∞ |

(3) 40 μL of 10% L-arabinose solution was added to the bacterial solution in Step 1, and shaken at 37° C. and 200 rpm for 40 min.

(4) The system obtained after reaction in Step 2 was desalted for 40 min using VSWP01300 MF-Millipore white MCE hydrophilic filter membrane with a smooth surface having a pore size of 0.025 um and a diameter of 13 mm.

(5) The bacterial solution obtained in Step 3 was centrifuged at 9000 rpm for 1 min. The supernatant was discarded, and the pellet was added to 500 μL of sterilized ddH$_2$O to re-suspend the bacterial solution. The bacterial solution was then centrifuged at 9000 rpm for 1 min. The supernatant was discarded. After the process was repeated twice, the supernatant was discarded, and the pellet was added to 50 μL of sterilized ddH$_2$O to re-suspend the bacterial solution and then allowed to stand on ice.

(6) The desalted solution obtained in Step 4 was uniformly mixed with the treated bacterial solution obtained in Step 5, and allowed to stand on ice for 1 min.

All the mixture was pipetted and subjected to electroporation (parameters: 1350 V, 200 Ω, 25 mA, 1 uF).

(8) 1 mL of fresh LB liquid medium (sterilized, containing no resistance screening agent) was added to the electroporation cuvette, beaten evenly, pipetted into an EP tube, and incubated at 37° C. and 200 rpm or 1 h.

(9) 50 μL of the bacterial solution was coated onto an LB plate containing 50-100 ug/ml Amp and incubated at 37° C. overnight.

(10) Single clones were picked up for verification by PCR and sequencing.

Example 2

Construction of PDC1 Knockout Cassette

By using the genome of *Saccharomyces cerevisiae* as a template, an upstream and a downstream 500 bp homology arm of the PDC1 fragment were amplified by using the primers PDC1UF/PDC1UR and PDC1DF/PDC1DR, and the G418 resistant gene fragment was amplified by using the primers G418F/G418R. A PDC1 knockout cassette was constructed by fusion PRC, and verified by sequencing.

Primer Sequences:

PDC1UF sequence as shown in SEQ ID NO. 13; PDC1UR sequence as shown in SEQ ID NO. 14; G418F sequence as shown in SEQ ID NO. 15; G418R sequence as shown in SEQ ID NO. 16; PDC1DF sequence as shown in SEQ ID NO. 17; and PDC1DR sequence as shown in SEQ ID NO. 18.

Example 3

Construction of TyrA Expression Cassette

By using the genome of *Saccharomyces cerevisiae* as a template and using the primers PDC1F-YZ/PDC1UF1 and the upstream 500 bp homology arm, and by using the pdc1 knockout cassette constructed in Example 2 as a template and using the primers G418F1/PDCIR-YZ, tyrA and the downstream 500 bp fragment of pdc1 were amplified. By using the genome of *Escherichia coli* BL-21(DE3) as a template and using the primers tyrAF1/tyrAR1, the tyrA gene fragment was amplified. A tyrA expression cassette was constructed by fusion PRC, and verified by sequencing.

Primer Sequences:

PDC1F-YZ sequence as shown in SEQ ID NO. 19; PDC1UF1 sequence as shown in SEQ ID NO. 20; TyrAF1 sequence as shown in SEQ ID NO. 21; TyrAR1 sequence as shown in SEQ ID NO. 22; G418F1 sequence as shown in SEQ ID NO. 23; and PDCIR-YZ sequence as shown in SEQ ID NO. 24.

Example 4

Construction of HpaBC Expression Cassette

The amino acid sequences as shown in SEQ ID NO. 5 and SEQ ID NO. 7 were codon-optimized according to the codon preference of the host *Saccharomyces cerevisiae*, to obtain optimized nucleotide sequences as shown in SEQ ID NO. 6 and SEQ ID NO. 8 corresponding to SEQ ID NO. 5 and SEQ ID NO. 7 for gene synthesis. A HpaBC expression cassette was constructed according to the method described in Example 1.

Example 5

Construction of Microbial Strains Heterologously Synthesizing Tyrosol, with *Saccharomyces cerevisiae* as an Example:

The strain obtained in Example 1 was inoculated in a liquid LB medium, and incubated at 37° C. and 200 rpm for 14 h, and then extracted with the OMEGA plasmid extraction kit D6943-01 to obtain the pJFE3-PcAAS-ADH recombinant expression plasmid. *Saccharomyces cerevisiae* BY4741 was transformed by the PEG/LiAc method. Single clones were screened by using the URA selective medium, and the plasmid was extracted. The clones were verified by PCR using the primers YZ1F and YZ1R to obtain the PcAAS-ADH strain. The PDC1 knockout cassette obtained in Example 2 and the TyrA expression cassette obtained in Example 3 were introduced into the PcAAS-ADH strain to obtain the PcAAS-ADH-ΔPDC1-TyrA strain. On the basis of the PcAAS-ADH-ΔPDC1-TyrA strain, the HpaBC expression cassette constructed in Example 5 was introduced into the PcAAS-ADH-ΔPDC1-TyrA strain by the PEG/LiAc method, to obtain the PcAAS-ADH-ΔPDC1-TyrA-HpaBC strain.

The YZ1F sequence is as shown in SEQ ID NO. 25; and the YZ1R sequence is as shown in SEQ ID NO. 26.

Example 6

Fermentation with Microorganisms Synthesizing Tyrosol, with *Saccharomyces cerevisiae* as an Example:

Single clones were picked up from a plate containing the PcAAS-ADH strain or PcAAS-ADH-ΔPDC1-TyrA strain producing tyrosol, inoculated to 5 mL of a selective medium for screening auxotrophic yeast, incubated at 30-32° C. and 200 rpm for 24 h, further inoculated in 50 mL of a selective medium for screening auxotrophic yeast at an initial OD600 of 0.2, incubated at 30° C. and 200 rpm for 12 h, and further inoculated in 100 mL of a selective medium for screening auxotrophic yeast at an initial OD600 of 0.2. Glucose, fructose, sucrose, glucose and tyrosine were respectively added for 72-h fermentation experiment. The tyrosol concentration in the fermentation broth was detected by the HPLC method reported in the literature (Satoh, Tajima et al. 2012). The amounts of tyrosol produced by culturing in the presence of various carbon sources are shown in Table 4.

TABLE 4

Amounts of tyrosol produced by 72-h fermentation in the presence of various carbon sources

| Strain (mg/L) | 2% glucose (mg/L) | 2% glucose + 1% tyrosine (mg/L) | 2% fructose (mg/L) | 2% sucrose (mg/L) |
| --- | --- | --- | --- | --- |
| PcAAS-ADH-ΔPDC1-TyrA | 1103.16 | 1326.18 | 964.72 | 724.37 |
| PcAAS-ADH | 941.42 | 846.96 | 1121.08 | 1038.11 |
| BY4741 | 34.33 | 35.65 | 38.32 | 36.54 |

Example 7

Fermentation with Microorganisms Synthesizing Hydroxytyrosol, with *Saccharomyces cerevisiae* as an Example:

Single clones were picked up from a plate containing the PcAAS-ADH-ΔPDC1-TyrA-HpaBC strain producing hydroxytyrosol, inoculated to 5 mL of a selective medium for screening auxotrophic yeast, incubated at 30-32° C. and 200 rpm for 24 h, further inoculated in 50 mL of a selective medium for screening auxotrophic yeast at an initial OD600 of 0.2, incubated at 30° C. and 200 rpm for 12 h, and further inoculated in 100 mL of a selective medium for screening auxotrophic yeast at an initial OD600 of 0.2 for 72-h fermentation experiment. The hydroxytyrosol concentration in the fermentation broth was detected by the HPLC method reported in the literature (Satoh, Tajima et al. 2012). 978 mg/L of hydroxytyrosol was obtained after 72-h fermentation.

The foregoing descriptions are merely preferred embodiments of this application, but are not intended to limit this application. A person of ordinary skill in the art may make various alterations and variations to this application. Any modification, equivalent replacement, or improvement made without departing from the spirit and principle of this application shall fall within the protection scope of this application.

What is claimed is:

1. A recombinant yeast comprising heterologous DNA sequences that encode SEQ ID NO: 1 and SEQ ID NO: 3 wherein the recombinant yeast is engineered to produce tyrosol.

2. The recombinant yeast according to claim 1, wherein the heterologous DNA sequences comprise SEQ ID NO: 2 and SEQ ID NO: 4.

3. The recombinant yeast according to claim 1, further comprising a cluster of heterologous DNA sequences derived from *Escherichia coli* that encode 4-hydroxyphenylacetic hydroxylase wherein the recombinant yeast is engineered to produce hydroxytyrosol.

4. The recombinant yeast according to claim 3, wherein the cluster of heterologous DNA sequences encodes SEQ ID NO: 5 and SEQ ID NO: 7.

5. The recombinant yeast according to claim 4, wherein the cluster of heterologous DNA sequences comprises SEQ ID NO: 6 and SEQ ID NO: 8.

6. A method for producing tyrosol comprising performing fermentation with the recombinant yeast according to claim 1 so as to obtain tyrosol, wherein a medium for the fermentation comprises any of glucose, fructose, sucrose, glucose or tyrosine.

7. A method for producing hydroxytyrosol comprising performing fermentation with the recombinant yeast according to claim 3 so as to obtain hydroxytyrosol, wherein the medium for the fermentation comprises any of glucose, fructose, sucrose, glucose or tyrosine.

* * * * *